(12) United States Patent
Fankhauser et al.

(10) Patent No.: US 10,602,911 B2
(45) Date of Patent: Mar. 31, 2020

(54) LOAD CARRIER FOR A CLEANING MACHINE

(71) Applicant: BELIMED AG, Zug (CH)

(72) Inventors: Simon Fankhauser, Grossaffoltern (CH); Dominik Brun, Kriens (CH); Jan Jenko, Lucerne (CH)

(73) Assignee: BELIMED AG, Zug (CH)

( * ) Notice: Subject to any disclaimer, the term of this patent is extended or adjusted under 35 U.S.C. 154(b) by 0 days.

(21) Appl. No.: 15/711,006

(22) Filed: Sep. 21, 2017

(65) Prior Publication Data

US 2018/0084968 A1    Mar. 29, 2018

(30) Foreign Application Priority Data

Sep. 29, 2016 (EP) .................................. 16191447

(51) Int. Cl.
*A47L 15/50* (2006.01)
*A61L 2/26* (2006.01)
*A61B 90/70* (2016.01)

(52) U.S. Cl.
CPC ........... *A47L 15/507* (2013.01); *A47L 15/508* (2013.01); *A61B 90/70* (2016.02); *A61L 2/26* (2013.01); *A61L 2202/24* (2013.01)

(58) Field of Classification Search
CPC .......... A47L 15/18; A47L 15/22; A47L 15/23; A47L 15/0076; A47L 15/0078; A47L 15/0081; A47L 15/507; A47L 15/50; A47L 15/508; A61L 2/26; A61L 2202/24
See application file for complete search history.

(56) References Cited

U.S. PATENT DOCUMENTS

| 6,622,740 B1 * | 9/2003 | Durazzani ........... A47L 15/0084 134/115 R |
| 6,869,029 B2 * | 3/2005 | Ochoa, Sr. ............ A47L 15/508 134/176 |
| 6,997,195 B2 * | 2/2006 | Durazzani ........... A47L 15/0084 134/198 |

(Continued)

FOREIGN PATENT DOCUMENTS

| DE | 35 34 838 A1 | 4/1987 |
| DE | 10 2008 011 743 A1 | 9/2009 |

(Continued)

OTHER PUBLICATIONS

European Search Report Corresponding to 16191447.8 dated Oct. 31, 2016.

*Primary Examiner* — Patrick D Hawn
(74) *Attorney, Agent, or Firm* — Davis & Bujold PLLC; Micheal J. Bujold

(57) ABSTRACT

A load carrier (1) for a cleaning machine is proposed. The load carrier (1) comprises a carrying frame with a lower load carrier tier (2) and an upper load carrier tier (3) which are arranged parallel to one another and which are connected to one another by spacers (5, 6). Furthermore, the load carrier (1) comprises at least one further, removable load carrier tier (11) which, parallel to the upper and lower load carrier tiers (2, 3), is detachably fastened to, preferably slidable into, the carrying frame. The removable load carrier tier (11) comprises a rotatably mounted wash arm (10) and at least one feed line (8) for the supply of a fluid to the wash arm (10).

11 Claims, 4 Drawing Sheets

(56) References Cited

U.S. PATENT DOCUMENTS

| | | | | |
|---|---|---|---|---|
| 8,709,172 B2* | 4/2014 | Casonato | | A47L 15/247 134/145 |
| 9,827,600 B2* | 11/2017 | Voyer | | B08B 3/024 |
| 2003/0163867 A1* | 9/2003 | Zhou | | A47K 3/286 4/599 |
| 2004/0007256 A1* | 1/2004 | Durazzani | | A47L 15/0084 134/57 D |
| 2007/0289615 A1* | 12/2007 | Shin | | A47L 15/23 134/56 D |
| 2009/0071514 A1* | 3/2009 | Roth | | A47L 15/485 134/56 D |
| 2010/0116296 A1* | 5/2010 | Bertsch | | A47L 15/16 134/25.2 |
| 2012/0111363 A1* | 5/2012 | Mohrbacher | | A47L 15/0031 134/10 |
| 2012/0175431 A1* | 7/2012 | Althammer | | B08B 3/024 239/263 |
| 2012/0279535 A1* | 11/2012 | Robert | | B01L 99/00 134/198 |
| 2012/0305037 A1* | 12/2012 | Petric | | A61B 90/70 134/198 |
| 2012/0312341 A1* | 12/2012 | Rieder | | B01L 99/00 134/198 |
| 2013/0152968 A1* | 6/2013 | Bertsch | | A47L 15/0013 134/18 |
| 2013/0180553 A1* | 7/2013 | Gaus | | A47L 15/483 134/105 |
| 2015/0239018 A1* | 8/2015 | Voyer | | B08B 3/024 239/264 |
| 2017/0135547 A1* | 5/2017 | Tuner | | A47L 15/0065 |
| 2017/0332879 A1* | 11/2017 | Gerstner | | A47L 15/503 |

FOREIGN PATENT DOCUMENTS

| | | | | |
|---|---|---|---|---|
| EP | 1 477 101 A2 | 11/2004 | | |
| EP | 1 929 927 A1 | 6/2008 | | |
| EP | 2452759 A1 | * 5/2012 | | B08B 3/024 |
| KR | 20020093512 A | * 12/2002 | | |

* cited by examiner

LOAD CARRIER FOR A CLEANING MACHINE

The present invention relates to a load carrier for a cleaning machine as per the preamble of Claim 1.

Cleaning machines of said type are used for the cleaning and disinfection of medical equipment. To enable the individual load carrier tiers to be laden with bulky articles, the load carrier tiers are often removable from the load carrier. The load carrier tiers are additionally equipped with a rotatably mounted wash arm which can be set in rotation by a fluid introduced into it, in order to improve the distribution of the fluid in a cleaning space of the cleaning machine.

The load carriers of the type mentioned in the introduction may be of modular construction. Depending on the products, load carrier tiers and/or wash arms with the associated feed line may be omitted. For example, DE 10 2008 011 743 A1 describes a flexibly configurable load carrier for a cleaning machine.

Situations however arise in which it is forgotten to install wash arms during the construction of the load carrier. The cleaning performance then does not meet the required standard, such that, if the error is discovered in the first place, batches must be cleaned and/or disinfected again. Such a repetition is time-consuming, expensive and energy-intensive.

It is an object of the present invention to overcome these disadvantages in the prior art. In particular, it is an object of the present invention to provide a device of the type mentioned in the introduction which permits improved operational reliability and substantially prevents incorrect manipulation.

The object is achieved by means of a load carrier having the features in Claim 1. The load carrier for a cleaning machine comprises a carrying frame with a lower load carrier tier and an upper load carrier tier which are arranged parallel to one another and which are connected to one another by spacers. Furthermore, the load carrier comprises at least one further, removable load carrier tier which, parallel to the upper and lower load carrier tiers, is detachably fastened to, preferably slidable into, the carrying frame. The removable load carrier tier comprises a rotatably mounted wash arm and at least one feed line for the supply of a fluid to the wash arm.

It is pointed out at this point that the removable load carrier tier does not imperatively need to be arranged between the upper and the lower load carrier tiers. The removable load carrier tier may for example be arranged above the upper load carrier tier.

By virtue of the fact that the load carrier tier itself comprises a wash arm and at least one feed line for the supply of a fluid to the wash arm, a situation in which it is forgotten to install one of the wash arms during the construction of the load carrier is ruled out by structural measures, because the wash arm and feed line are always removed and reinserted with the removable load carrier tier, in particular jointly (that is to say in a single working step). Incorrect manipulation during the use of the load carrier is thus substantially prevented. Constant cleaning performance which meets the standards is ensured at all times.

The load carrier tiers may have a-substantially rectangular shape, wherein the spacers are arranged at the corners of the load carriers and perpendicular thereto. Since the cleaning spaces of most cleaning machines have a rectangular base area, this design of the load carrier tiers achieves optimum space utilization. The stated arrangement of the spacers also allows the greatest possible number of pieces of medical equipment to be accommodated on one load carrier tier.

At least one spacer may comprise a fluid line. In this way, fluid can be conveyed from a first load carrier tier to a second. The fluid line may be equipped with connector means for the feed line of the removable load carrier tier.

The removable load carrier tier may be equipped with two feed lines. In this way, the cross section of the individual feed line can be selected to be smaller, which permits space savings with regard to the connector means for the feed line. Furthermore, a supply of fluid to the wash arm remains ensured in the event of failure of one feed line.

The axis of rotation of the wash arm may run through the intersection point of the diagonals of the associated load carrier tier. In this way, an ideal distribution of the fluid in the cleaning space of the cleaning machine is achieved.

In particular, the upper load carrier tier may comprise a rotatably mounted wash arm and at least one feed line for the supply of a fluid to the wash arm.

A load carrier of the above-stated type may comprise a middle load carrier tier which is arranged fixedly between the lower and the upper load carrier tiers, wherein in each case one removable load carrier tier is arranged between the lower and the middle and between the middle and the upper load carrier tiers. This embodiment has proven to be advantageous in practice for the cleaning and disinfection of frequently used medical equipment with regard to the size thereof.

A connector piece for the supply of a fluid from the cleaning machine to the wash arm may be arranged below the lower load carrier tier.

The load carrier tier may be mounted displaceably on rails of the load carrier. This facilitates the removal of the load carrier tier. The rails may be designed as substantially L-shaped profile projections of the load carrier tier arranged thereabove.

The invention will be described in more detail below on the basis of an exemplary embodiment and in conjunction with the drawing.

In the drawing, in each case schematically:

Figure 1:
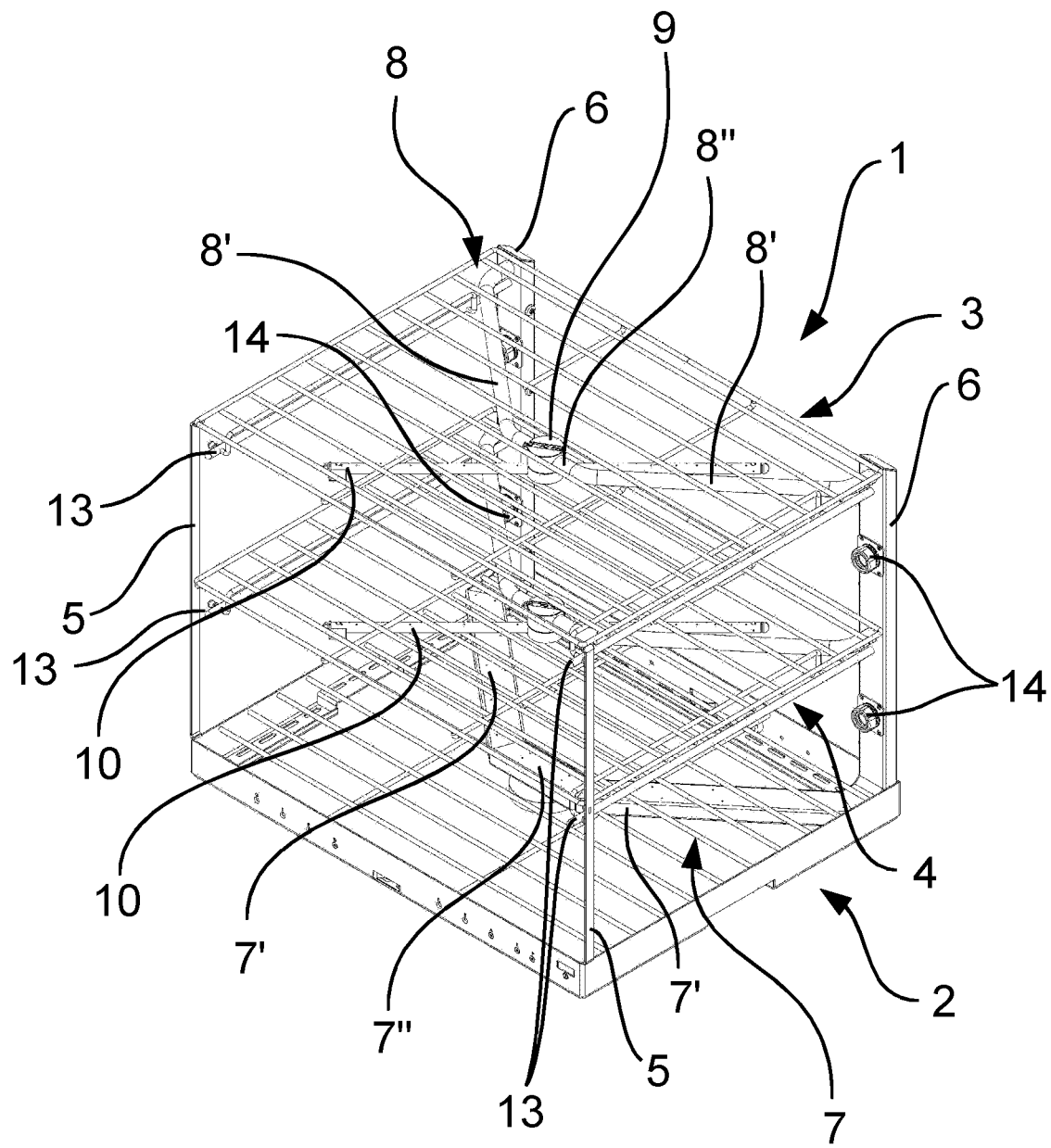
FIG. 1 shows a perspective view of a load carrier according to the invention without intermediate tiers.

FIG. 1 shows a load carrier 1. Said load carrier is made up of three load carrier tiers, specifically a lower load carrier tier 2, an upper load carrier tier 3 and a middle load carrier tier 4 arranged in between. The load carrier tiers 2, 3 and 4 are formed as grates and are arranged parallel to one another and so as to be equally spaced apart from one another.

At the corners of the rectangular load carrier tiers 2, 3 and 4, there run supports 5 and 6 which serve as spacers and which connect the load carrier tiers 2, 3 and 4 fixedly to one another. The supports 5 are formed as simple rods. The supports 6 are of hollow form and serve for the feed of operating liquid.

Below the lower load carrier tier there is arranged an infeed device 7 for the operating liquid. Said infeed device 7 is composed of two diagonally running, hollow sections 7' which are connected in fluid-conducting fashion to the respective support 6. In the region of the intersection point of the diagonals of the lower load carrier tier 2, there is arranged a central section 7" which is equipped with an inflow connector (not visible) for the operating liquid. When the load carrier is situated in a cleaning machine, a fluid-conducting connection to the diagonal sections 7' and consequently to the supports 6 can be produced by means of the central section 7" of the infeed device 7.

By contrast, the upper load carrier tier 3 and the middle load carrier tier 4 have a feed line 8, wherein, for the sake of clarity, only the feed line 8 of the upper load carrier tier 3 is denoted by a reference designation. The feed line 8 is likewise made up of two diagonally running sections 8', which are suspended on the respective load carrier tier, and of a central section 8" which is arranged in the region of the intersection point of the diagonals of the respective load carrier tier. The central section 8" furthermore comprises a suspension device 9 for a wash arm 10.

The respective wash arm 10 of a load carrier tier can thus be supplied with operating liquid, and set in rotation, via the infeed device 7 and the hollow supports 6 and via the feed line 8.

Figure 2:
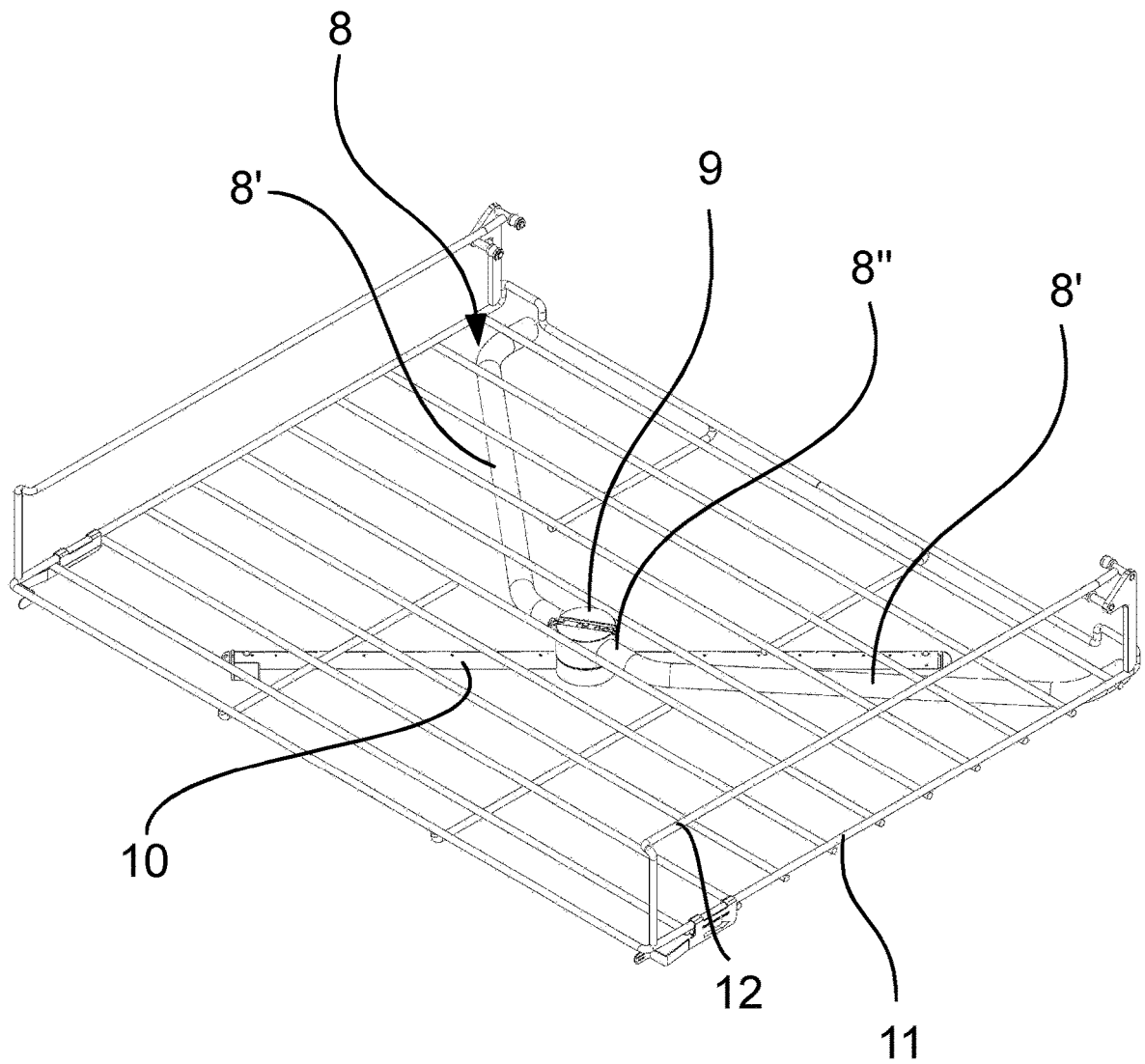
FIG. 2 shows a perspective view of an intermediate tier without wash arm.
Figure 3:
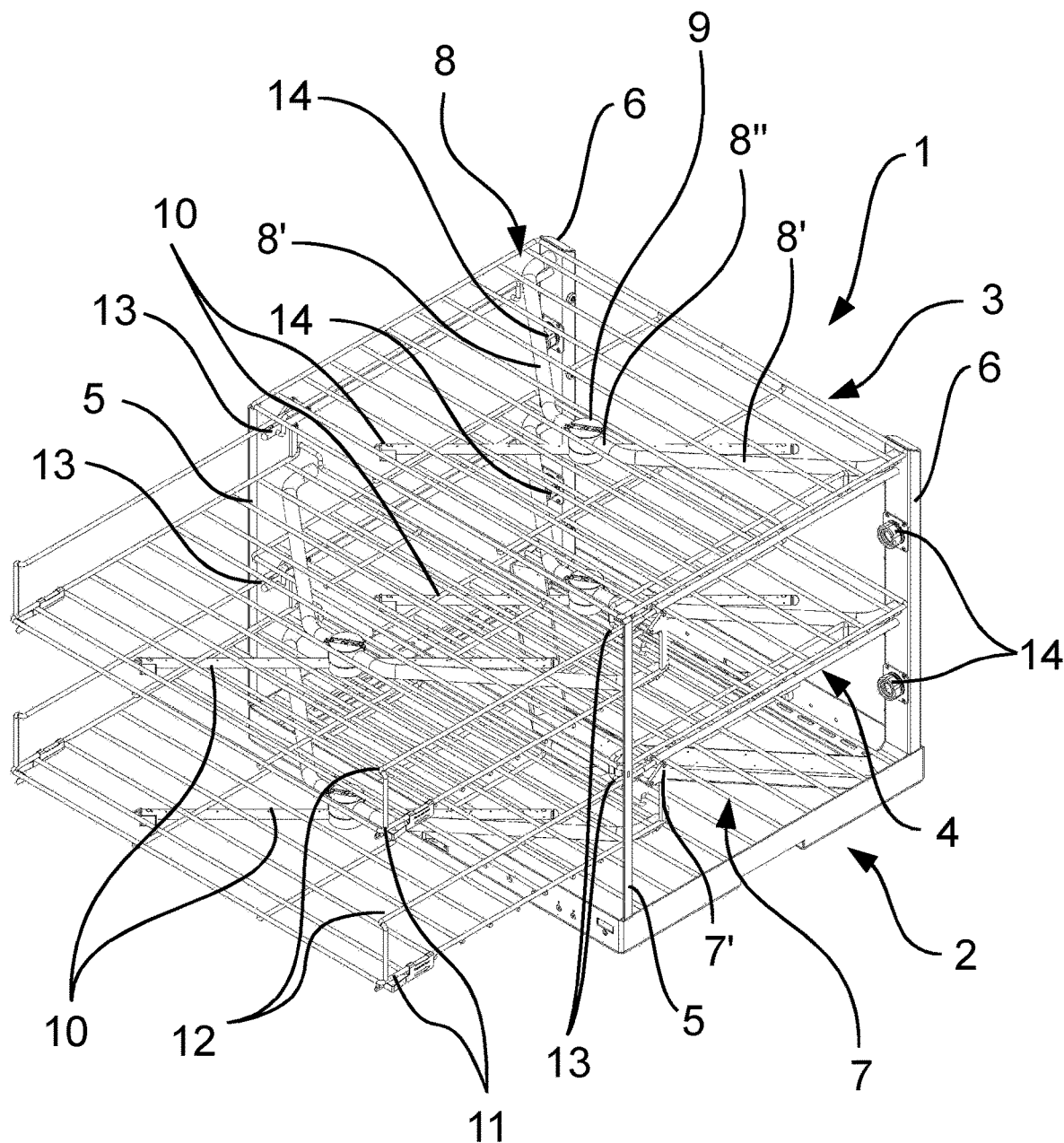
FIG. 3 shows a perspective view of the load carrier from FIG. 1 with pulled-out intermediate tiers.

FIG. 2 shows an intermediate tier 11. The intermediate tier 11 is of similar construction to the load carrier tiers 2, 3 and 4 and likewise comprises a feed line 8, a suspension device 9 and a wash arm 10. The intermediate tier 11 however comprises, at the shorter edges, in each case one bracket 12 which protrudes out of the plane of the intermediate tier 11.

The upper load carrier tier 2 and the middle load carrier tier 3 each have, on their underside, a suspended rail 13. The rails 13 and the brackets 12 are designed so as to complement one another, such that the intermediate tier 11 is arranged so as to be displaceable in the tanner of a drawer along the rail 13, such that a removal of the intermediate tier 11 for the purposes of loading bulky articles onto the lower load carrier tier 2 and/or onto the middle load carrier tier 4 is made possible.

In the event of a removal from the load carrier 1, the feed line 8 and the wash arm 10 are also removed, as illustrated in FIG. 2. A situation in which the wash arm 10 is forgotten is thus ruled out.

Since the load carrier 1 can be used with or without intermediate tiers 11, valve arrangements 14 are provided on the supports 6, which valve arrangements firstly make it possible for a fluid-conducting connection to be established between the support 6 and the wash arm 10 of the intermediate tier 11, and secondly prevent the operating liquid from being able to flow out of the supports 6 when no intermediate tier is inserted. The valve arrangements 14 are formed in the manner of check valves or of self-closing flaps, such that the fluid pressure prevailing in the supports 6 seals off the valve arrangement to the outside when no intermediate tier is inserted and consequently no feed line 8 is inserted into the valve arrangement 14.

Figure 4:
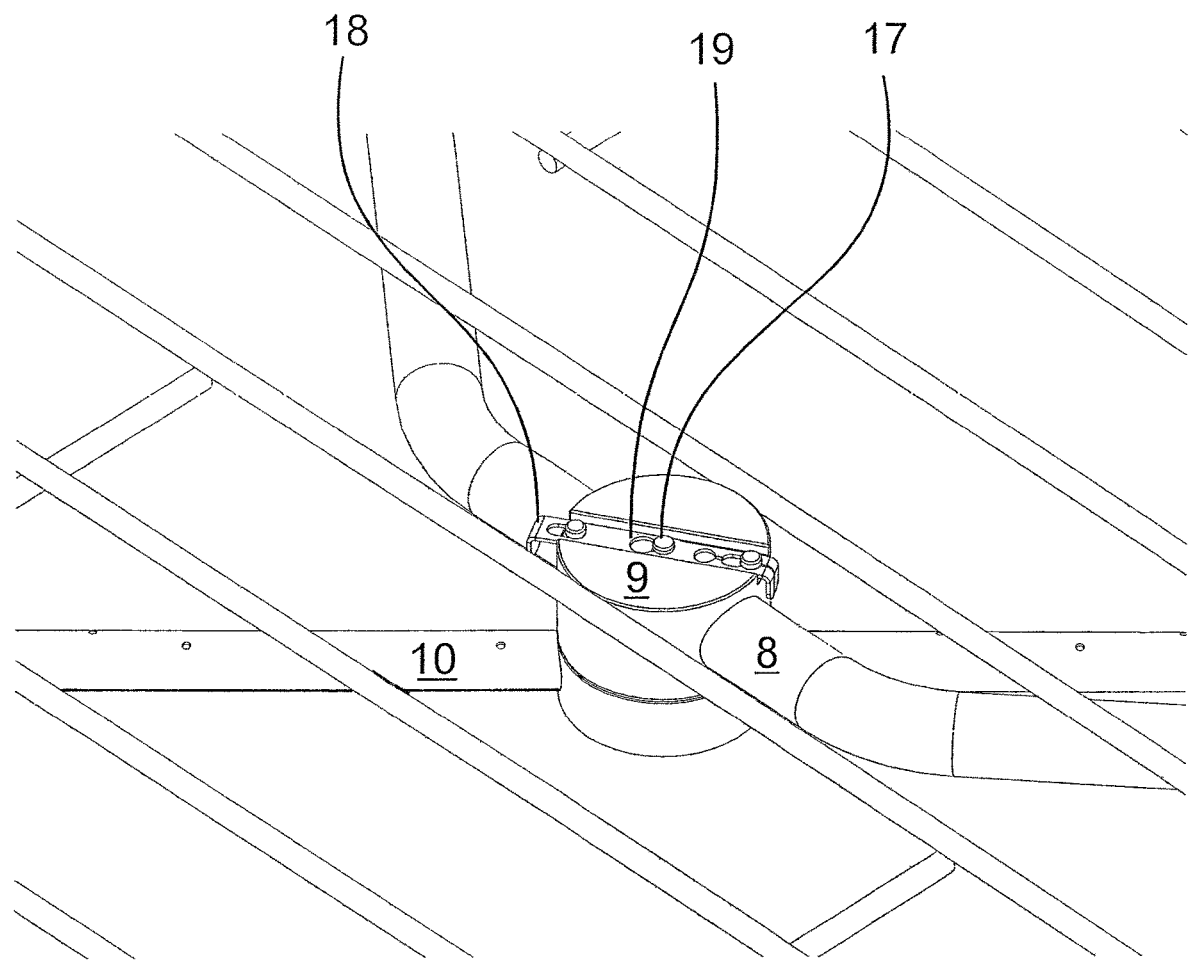
FIG. 4 shows a detail view of the wash arm suspension.

FIG. 4 shows a detail view of the suspension device 9 for a wash arm 10. The wash arm is suspended by means of a bolt 17 which extends through the suspension device 9. On the suspension device 9 there is provided a securing slide 18 which is movable back and forth between a release position and a closed position. The securing slide has an opening 19 with a keyhole-like profile. With the securing slide 18 in the release position, the bolt 17 can be removed from the suspension device 9, because the opening 19 corresponds to the bolt cross section. With the securing slide 18 in the closed position (and with the bolt 17 inserted), however, the narrow section of the opening 19 is engaged into a groove of the bolt 17, and the wash arm 10 is thus suspended.

The invention claimed is:

1. A load carrier for a cleaning machine, comprising:
   a carrying frame having at least three load carrier tiers, wherein the load carrier has no wall over an entire side of the load carrier;
   a lower load carrier tier and an upper load carrier tier are arranged parallel to one another and are connected to one another by spacers;
   the spacers are formed as rods;
   each rod is spaced horizontally from the other rods;
   the rods fixedly connect the lower load carrier tier and the upper load carrier tier with one another;
   at least one rod is hollow and comprises a fluid line;
   at least one further, removable load carrier tier which, parallel to the upper and lower load carrier tiers, is detachably fastened, via rails, to the carrying frame;
   the removable load carrier tier comprises a rotatably mounted wash arm and at least one feed line for the supply of a fluid to the wash arm;
   the load carrier is adapted to be situated in a cleaning machine; and
   the rails are designed as substantially L-shaped profile projections of the load carrier tier arranged there above.

2. The load carrier according to claim 1, wherein the removable load carrier tier is slidable into the carrying frame.

3. The load carrier according to claim 1, wherein the wash arm and the at least one feed line are removable and reinsertable jointly with the removable load carrier tier.

4. The load carrier according to claim 1, wherein the load carrier tiers have a substantially rectangular shape, and wherein the spacers are arranged at the corners of the load carrier tiers and perpendicular thereto.

5. The load carrier according to claim 1, wherein the fluid line is equipped with connector means for the feed line of the removable load carrier tier.

6. The load carrier according to claim 5, wherein the removable load carrier tier is equipped with two feed lines.

7. The load carrier according to claim 4, wherein the axis of rotation of the wash arm runs through the intersection point of the diagonals of the associated load carrier tier.

8. The load carrier according to claim 1, wherein the upper load carrier tier comprises a rotatably mounted wash arm and at least one feed line for the supply of a fluid to the wash arm.

9. The load carrier according to claim 1, wherein said load carrier comprises a middle load carrier tier which is arranged fixedly between the lower and the upper load carrier tiers (2, 3), and wherein in each case one removable load carrier tier is arranged between the lower and the middle and between the middle and the upper load carrier tiers.

10. The load carrier according to claim 1, wherein a connector piece for the supply of a fluid from the cleaning machine to the wash arm is arranged below the lower load carrier tier.

11. The load carrier according to claim 1, wherein the removable load carrier tier is mounted displaceably on the rails of the load carrier (1).

* * * * *